US006802460B2

(12) United States Patent
Hess et al.

(10) Patent No.: US 6,802,460 B2
(45) Date of Patent: Oct. 12, 2004

(54) METHOD AND SYSTEM FOR AMBIENT AIR SCENTING AND DISINFECTING BASED ON FLEXIBLE, AUTONOMOUS LIQUID ATOMIZER CARTRIDGES AND AN INTELLIGENT NETWORKING THEREOF

(75) Inventors: Joseph Hess, Bevaix (CH); Myriam Muller, Dudeldange (LU)

(73) Assignee: Microflow Engineering SA, Neuchatel (CH)

( * ) Notice: Subject to any disclaimer, the term of this patent is extended or adjusted under 35 U.S.C. 154(b) by 322 days.

(21) Appl. No.: 10/087,924

(22) Filed: Mar. 5, 2002

(65) Prior Publication Data

US 2003/0168524 A1 Sep. 11, 2003

(51) Int. Cl.[7] .............................................. A01G 27/00
(52) U.S. Cl. ................. 239/306; 239/102.2; 239/102.1; 239/4; 239/69; 239/338; 239/328; 239/303
(58) Field of Search ................................ 239/306, 338, 239/73, 102.1, 102.2, 310, 398, 418, 423, 4, 69, 328, 303, 304; 222/145.6, 145.1, 145.5, 105, 94, 136

(56) References Cited

U.S. PATENT DOCUMENTS

| | | | |
|---|---|---|---|
| 3,044,276 A | 7/1962 | Kauten | 62/311 |
| 3,677,441 A | 7/1972 | Nixon, Jr. et al. | 222/63 |
| 3,960,324 A | * 6/1976 | Titus et al. | 239/4 |
| 4,467,961 A | 8/1984 | Coffee et al. | 239/1 |
| 4,530,464 A | * 7/1985 | Yamamoto et al. | 239/102.2 |
| 4,605,167 A | * 8/1986 | Maehara | 239/102.2 |
| 4,667,877 A | * 5/1987 | Yao et al. | 239/102.2 |
| 4,826,048 A | * 5/1989 | Skorka et al. | 222/137 |
| 5,038,972 A | 8/1991 | Muderlak et al. | 222/25 |
| 5,046,648 A | 9/1991 | Herbstzuber | 222/638 |
| 5,147,582 A | 9/1992 | Holzner, Sr. et al. | 261/30 |
| 5,178,327 A | 1/1993 | Palamand et al. | 239/57 |
| 5,186,869 A | 2/1993 | Stumpf et al. | 261/30 |
| 5,223,182 A | 6/1993 | Steiner et al. | 261/26 |
| 5,342,584 A | 8/1994 | Fritz et al. | 422/124 |
| 5,431,859 A | 7/1995 | Tobin | 261/52 |

(List continued on next page.)

FOREIGN PATENT DOCUMENTS

| | | |
|---|---|---|
| EP | 0 714 709 A1 | 6/1996 |
| EP | 0 831 384 A1 | 3/1998 |
| EP | 0 923 957 A1 | 6/1999 |
| EP | 1 184 083 A1 | 3/2002 |
| EP | 1 287 905 A1 | 3/2003 |
| FR | 2 776 947 | 4/1998 |
| WO | WO-00/38512 A1 | 7/2000 |
| WO | WO-00/47335 A1 | 8/2000 |
| WO | WO-02/09772 A2 | 2/2002 |
| WO | WO-02/09773 A2 | 2/2002 |
| WO | WO-02/09776 A2 | 2/2002 |
| WO | WO-02/09779 A1 | 2/2002 |
| WO | WO 02/068128 A2 | 9/2002 |

*Primary Examiner*—Patrick Brinson
(74) *Attorney, Agent, or Firm*—Griffin & Szipl, P.C.

(57) ABSTRACT

An apparatus for freshening air, including a base unit; a power supply operably connected to the base unit; a driving and switching circuit connected to be powered by the power supply; a first plug portion connected to the driving and switching circuit; a detachable autonomous liquid droplet dispensing cartridge detachably engagable with the first plug portion. The detachable cartridge has (a) a second plug portion matingly engagable with the first plug portion, (b) a first airless bag for storing a first nebulizable liquid, (c) a second airless bag for storing a second nebulizable liquid, and (d) a casing enclosing the first bag and the second bag. A nebulizer is provided so that a first nebulizable liquid flows from the first bag and the second nebulizable liquid flows from the second bag so that the first nebulizable liquid and the second nebulizable liquid are nebulized by the nebulizer.

17 Claims, 7 Drawing Sheets

U.S. PATENT DOCUMENTS

| | | | | |
|---|---|---|---|---|
| 5,518,179 A | * | 5/1996 | Humberstone et al. | 239/102.2 |
| 5,529,055 A | | 6/1996 | Gueret | 128/200.16 |
| 5,549,247 A | | 8/1996 | Rossman et al. | 239/57 |
| 5,591,409 A | | 1/1997 | Watkins | 422/110 |
| 5,601,235 A | * | 2/1997 | Booker et al. | 239/4 |
| 5,760,873 A | | 6/1998 | Wittek | 352/85 |
| 5,832,320 A | | 11/1998 | Wittek | 396/106 |
| 5,938,117 A | | 8/1999 | Ivri | 239/4 |
| 6,062,430 A | | 5/2000 | Fuchs | 222/105 |
| 6,110,888 A | | 8/2000 | Lupo, Jr. et al. | 512/1 |
| 6,196,219 B1 | * | 3/2001 | Hess et al. | 128/200.21 |
| 6,267,297 B1 | | 7/2001 | Contadini et al. | 239/1 |
| 6,293,474 B1 | | 9/2001 | Helf et al. | 239/102.2 |
| 6,305,578 B1 | * | 10/2001 | Hildebrandt et al. | 222/135 |
| 6,357,671 B1 | * | 3/2002 | Cewers | 239/102.2 |
| 6,405,934 B1 | * | 6/2002 | Hess et al. | 239/4 |
| 6,554,203 B2 | * | 4/2003 | Hess et al. | 239/69 |
| 6,722,582 B2 | * | 4/2004 | Hess et al. | 239/102.2 |

* cited by examiner

METHOD AND SYSTEM FOR AMBIENT AIR SCENTING AND DISINFECTING BASED ON FLEXIBLE, AUTONOMOUS LIQUID ATOMIZER CARTRIDGES AND AN INTELLIGENT NETWORKING THEREOF

FIELD OF THE INVENTION

The present invention relates to a method and apparatus for refreshing and disinfecting air streams. More particularly, the invention relates to refreshing and disinfecting air streams flowing into or through an environment or room by dispersing a fragrant disinfectant. Still more particularly, the present invention relates to a method and apparatus for refreshing and disinfecting air streams wherein a fragrance, a disinfectant, or other functional liquid is nebulized into an air stream, and the rate of nebulization of the liquid is controlled and determined by personal preferences of a user.

Moreover, in the present context, the term "freshening" means either scenting, disinfecting, or scenting and disinfecting, such as for an air stream or a body of air.

Note that for the purpose of this disclosure the terms "nebulized" and "atomized" will be considered equivalent and interchangeable.

BACKGROUND OF THE INVENTION

Scenting and disinfecting of ambient air in human living spaces has been an endeavor since ancient times. Several natural fragrance molecules have both scenting as well as disinfecting properties. In modem times, man has invented many ways of introducing the comfort of improved ambient air in personal, housing and working environments. In recent decades, home and working environments have evolved into tighter closed air systems, which largely re-circulate stale air including airborne particles and microorganisms trapped within these closed environments. Consequently, these closed air environments serve as pockets of particle accumulation (e.g., dust and pollen) and provide a potential growth medium for pathogenic and non-pathogenic microorganisms. Humans presently spend about 90% of their time inside enclosed spaces (i.e., rooms) in homes, hotels, offices, cars, airplanes, restaurants, etc. Much attention has been paid to determining the effects of indoor air quality on the health, comfort, and productivity of the inhabitants. Concepts such as "Sick Building Syndrome" (SBS) and "Perceived Air Quality" have been developed and have become issues of concern to the scientific, technical and financial communities. It is noted that the general notion of "Indoor Air Quality" (IAQ) includes the concepts of (a) ambient air scenting, (b) combating odors and (c) disinfecting. The present invention endeavors to provide an air refreshing solution addressing these issues.

To address the problems inherent to recirculating particle laden and microbe bearing air, the air-conditioning system was recognized early as a means of introducing deodorants, insecticides, moisturizers, bactericides, etc., into an air conditioning stream and thus treating ambient air. One such air-conditioning system is disclosed in U.S. Pat. No. 3,044,276 to Kauten.

More recent developments relate to dispersing volatiles (i.e., deodorants, insecticides, moisturizers, bactericides, etc.) into the air by the use of a so-called ion wind or ion drag which causes the molecules of the volatiles to be charged and to attach to other particles or bodies in the air such as dust, microorganisms or insects, but also to carpets, furniture, people and pets. (see WO 00/38512)

The combination of antimicrobial and scenting or flavoring capability in industrial compounds has also been previously disclosed as, for example, in U.S. Pat. No. 6,110,888 to Lupo et al.

Most recently, environmental concerns have attracted attention to the quality of ambient air in general, and HVAC systems in particular. Microorganisms, such as mold spores and bacteria, develop well within an environment which is prone to condensation by providing moisture and warmth, and which offers a lot of "dead volume" or space to settle in. However, a significant number of these microorganisms become airborne during the inherent carrier function of HVAC systems. Consequently, according to the Environmental Protection Agency (EPA), a significant amount of human respiratory problems are related to indoor air pollution (EPA Document Reference Number 402-R-94-007, 1994 and many others).

The term "air quality" can be more broadly interpreted, however. In addition to considering the numbers of particles and microbes in the air, "air quality" also relates in scope to encompass a more hedonistic component of air quality such as air scenting for providing relaxing, stimulating, romantic, etc., characteristics or simply for combating bad odors. Consequently many developments relate to this field of endeavor, such as those disclosed in U.S. Pat. No. 6,267,297 B1 to Contadini et al; U.S. Pat. No. 5,178,327 to Palamand et al.; U.S. Pat. No. 5,549,247 to Rossman et al.; U.S. Pat. No. 5,431,859 to Tobin et al.; U.S. Pat. No. 342,584 to Fritz et al.; U.S. Pat. No. 5,223,182 to Steiner et al.; U.S. Pat. No. 5,186,869 to Stumpfet al.; U.S. Pat. No. 5,147,582 to Holzner et al.; U.S. Pat. No. 5,038,972 to Muderlak et al.; U.S. Pat. No. 3,677,441 to Nixon et al.; and U.S. Pat. No. 5,591,409 to Watkins.

Most of these disclosed systems rely on some method of controlled scent release by actuation of aerosol cans, by venting air over gel-containing cartridges, or by evaporating scented liquids. More recently disclosed documents teach the use of modern dispensing methods for various liquid substances, which avoid the use of propellant gases. Indeed, some aerosol propellants may negatively affect air quality because their "Volatile Organic Component" (VOC) content and impact may raise related health questions in a manner similar to problems raised with chlorofluorocarbons (CFC's), which were previously used as propellants. Methods and apparatuses that avoid the use of propellant gases include U.S. Pat. No. 5,529,005 to Gueret, U.S. Pat. No. 6,293,474 B1 to Helf et al.; U.S. Pat. No. 5,938,117 to Ivri; U.S. Pat. No. 6,196,219 B1 to Hess et al., and more recently EP 01 121 075.4, to Hess et al. These various patents disclose the use of piezo-electric actuation in various configurations to effectively expel liquids without the use of propellants. The advantage of these piezo-electric systems is the excellent rendering and dispersion of scents by expelling small volumes of unaltered liquid substance into the ambient air followed by the efficacious diffusion of the scents due to the production of a large number of extremely small liquid droplets, which dramatically reduces the amount of both fragrance and solvent needed to provide a given scenting result, when compared to the other methods mentioned above. The main problem remaining with most of the devices above, however, is that reliable priming is not achieved and that these devices do not have the ability to function properly in every position within the realm of three-dimensional movement. In addition, the prior art piezoelectric scenting devices do not reliably operate over a wide range of viscosities and surface tensions of the liquid to be expelled by the piezoelectric element. Furthermore, the prior art devices have not been able to mix nebulizable liquids from multiple separate source reservoirs.

Consequently, many desirable liquids used in the piezo-electric prior art devices require the addition of a solvent or solvents in order to be sprayed by these devices. The result of using a solvent is that, at least to some degree, there remain health and air quality issues when a solvent is used. For example, Martens et al. teach, in document WO 00/47335, that the viscosity and surface tension of a liquid to be dispensed can be controlled by adding certain solvents, thereby providing a method of improving the dispensing action of piezo-actuated systems. Although it may be difficult to avoid such solvents completely in order to adequately disperse certain liquids, it is a reasonable objective to minimize the use of solvents.

Further sophisticated techniques and devices directed to ambient air scenting and disinfecting are disclosed in other documents which teach the use of modem electronics in circuits essentially used in the methods of timing, sequencing and dosing of a dispensed medium into various ambient living environments such as home care environments, home entertainment environments, scenting in cars, shopping, lodging, and public entertainment environments. In some cases, scent sensors are used in the electronic control circuitry of the scenting and air freshening devices in order to control the release of the scents and their intensity in the respective environment as disclosed in French document FR 98 04156 to Moy et al.; U.S. Pat. No. 5,591,409 to Watkins; European document EP 0 831 384 A1 to Muyarama et al.; U.S. Pat. Nos. 5,832,320 and 5,760,873, both to Wittek; and European document EP 00 118 715.2 and corresponding U.S. patent application Ser. No. 09/942,118, both to Hess et al. Specifically, EP 00 118 715.2 and U.S. patent application Ser. No. 09/942,118 are incorporated by reference in their entirety herein.

Another problem with some of the disclosed prior devices and systems is that they are subject to condensation effects due to extensive ducting, which inevitably occurs as a result of ambient temperature differences, condensation in ducts, pollution or contamination caused by growth of micro-organisms, etc. Another problem with some of the prior devices is that they are cumbersome to program and difficult to install or to network in a modem living, lodging or entertainment environment. Some prior devices have the drawback that they rely on artifacts, such as autonomous heating or ventilation processes, in the immediate vicinity of the dispensing unit. Some prior devices do not offer enough structural flexibility in order to satisfy the need for both a desired functionality and attractive design. Another major drawback with the prior devices is that all are very much orientation or position dependent. Yet another common drawback to the prior devices is that the control functions are more or less reduced to timing and sequencing of the scenting activity, which leaves the user little or no possibility to treat different scents in a different way according to his or her environment and his or her own sensitivity. In other words, the prior devices generally do not permit preferential selection of a particular scent in response to environmental parameters and/or the personal preference of the user at a particular time.

Another drawback with most of the prior devices is that they do not meet the needs created by today's rapidly changing environmental entertainment technologies. For instance, the home environment as well as the working, lodging and entertainment environments are rapidly changing to provide new entertainment and work tools that are readily available to a growing "on-line" population of information technology users in the home and outside of the home through the use of narrow—and broadband wireless systems, web-appliances, portable communication systems, PDA's, PC's, etc., that include separate and new smart wireless devices, "net-meeting" products, home "video-meeting" products, and products that permit downloading all sorts of entertainment pieces, etc. To a limited extent, the new demand for air scenting and refreshing in these entertainment and work environments has been partially addressed by devices disclosed in EP 0 714 709 A1 to Millet et al; U.S. Pat. Nos. 5,832,320 and 5,760,873 to Wittek, and by the devices disclosed in U.S. patent application Ser. No. 09/942,118 and European document EP 01 1118 715.2, both to Hess et al., but none of these devices introduces a user friendly, industrially applicable, practical and rapidly deployable solution to all of the aforementioned drawbacks and none allows the user to participate in an interactive manner with a network.

One attempt to provide ambient scenting to augment a "theme" of an entertainment environment is disclosed in WO 00209776, WO 00209773, WO 00209772, which relates scenting activity to a thematic sensory experience, such as experienced during music, graphic arts, theater and the like, by using a CD-like scent cartridge selection technology. However, the scenting technology used has been known for a long time and the disc-like arrangement is relatively rigid, and re-usable only at the disc level; thus giving the user little flexibility, albeit a lot of choices, as far as themes are concerned. It is unlikely that any individual user will like all of the 7 fragrances contained in the above rigidly arranged disk to the same degree so that all 7 fragrances will be used up in a similar manner and time frame. Most likely, only one or a few scents will be preferred, so that the corresponding scent-containing cartridges will be used up quickly, whereas one or a few other fragrances might not be liked at all. As can be easily appreciated, the preferential use of one or several fragrances will lead to the wasteful situation where the whole disk will be disposed of because the preferred fragrances have been exhausted and the remaining excess of the non-preferred fragrances with their solvent contents are left unused.

Consequently, there exists a need for a scenting and refreshing apparatus and method that overcomes the drawbacks of the prior devices and which satisfies the public need for wholesome air quality that is both safe and pleasing to the nose, and that provides a sense of personal comfort while addressing individual personal preferences. Specifically, there is a need for a scenting and refreshing apparatus and method that hedonistically augments air quality and which can be applied to the recent emergence of entertainment and work environments associated with web appliances, portable electronic devices, downloading of entertainment and work applications, and smart home environments.

It is therefore an objective of the present invention to overcome the drawbacks of the prior devices, which include excessive bulkiness, lack of flexibility, lack of modular and integrated packaging of cartridge and dispenser, lack of scenting and refreshing efficacy, lack of priming reliability, lack of an easy networking capability for programmable scenting or disinfecting capabilities, and lack of ease of use when dealing efficiently with habituation and the need to replace or exchange scents.

It a further object of the present invention to minimize the use of solvents as much as possible.

It is yet another object of the present invention to provide a scenting and refreshing apparatus and method which allows freedom to apply the apparatus and method to a variety of air quality, safety, personal environment and entertainment oriented applications.

It is another object of the present invention to provide an air scenting and refreshing apparatus and method that involves the user in an interactive role as part of these air quality, safety, personal environment and entertainment-oriented applications.

It is yet another object of the air scenting and refreshing apparatus and method of the present invention to permit the user to create a network with a web appliance, portable electronic device, downloaded entertainment or work application, or a smart home environment that can be manipulated by the user to satisfy particular environmental and other preferences of the user.

It is yet another object of the air scenting and refreshing apparatus and method of the present invention to provide for maximum scent choice flexibility, on the one hand, while minimizing waste and use of harmful ingredients (e.g., solvents), on the other hand.

It is yet another object of the invention to provide an air scenting and refreshing apparatus that mixes two liquids together at the time of nebulization or just prior to the moment that the mixed liquids will be nebulized.

SUMMARY OF THE INVENTION

In accordance with the above objectives, the present invention provides, in a first preferred embodiment, an apparatus for freshening air, including: a base unit; a power supply operably connected to the base unit; a driving and switching circuit connected to be powered by the power supply; a first plug portion connected to the driving and switching circuit; and a detachable autonomous liquid droplet dispensing cartridge detachably engagable with the first plug portion. The detachable cartridge has (a) a second plug portion matingly engagable with the first plug portion, (b) a first airless bag for storing a first nebulizable liquid (c) a second airless bag for storing a second nebulizable liquid, and (d) a casing enclosing the first bag and the second bag. A nebulizer is provided connected to each bag by a respective inlet of an interface, so that, when the nebulizer operates, and first and second nebulizable liquids are contained in the first and second bags, respectively, the first nebulizable liquid flows from the first bag and the second nebulizable liquid flows from the second bag, so that the first nebulizable liquid and the second nebulizable liquid are mixed in a space before being nebulized into a combined mist by the nebulizer. The nebulizer is electrically connected to the power supply and controlled by the driving and switching circuit when the second plug portion is matingly engaged to the first plug portion.

In accordance with a second preferred embodiment of the present invention, the first preferred embodiment is made to further comprise an interface that includes a first inlet that provides a path of egress for the first liquid and a second inlet that provides a path of egress for the second liquid, so that, when the nebulizer operates, and first and second nebulizable liquids are contained in the first and second bags, respectively, the first nebulizable liquid and the second nebulizable liquid flow from the first bag and the second bag, respectively, through the interface and into the nebulizer.

In accordance with third and fourth embodiments of the present invention, the apparatus of the first embodiment is made so that the nebulizer includes a nozzle membrane that has at least one nozzle sized to disperse droplets that are about 1–7 microns in diameter in the third embodiment and the nozzle membrane is made to have at least one nozzle sized to disperse droplets that are about 5–30 microns in diameter in the fourth preferred embodiment.

In a fifth preferred embodiment of the present invention, to the elements of the second preferred embodiment is included a switch that is disposed in the driving and switching circuit, and electrically connected to the power supply, wherein the switch activates the nebulizer and the flow of the first nebulizable liquid and the second nebulizable liquid from the first airless bag and the second airless bag respectively through the interface and into the nebulizer.

In a sixth preferred embodiment of the present invention, the switch of the apparatus of the fifth preferred embodiment is made to be operable by a remote unit. In a seventh preferred embodiment of the present invention, the remote unit of the sixth preferred embodiment is made to be a wireless control unit, a personal digital assistant, a cell phone, or a web-appliance.

In an eighth preferred embodiment of the present invention, the remote unit of the sixth preferred embodiment is made to include a turbulence sensor for sensing the flow of ambient air and a logarithmic gas sensor for detecting the combined concentration of the first nebulizable liquid and the second nebulizable liquid in the ambient air.

In a ninth preferred embodiment of the present invention, the first preferred embodiment is made so that the first bag contains a first nebulizable liquid that is different from a second nebulizable liquid contained in the second bag.

In a tenth preferred embodiment of the present invention, the ninth preferred embodiment is made so that the first nebulizable liquid is a primary fragrance and the second nebulizable liquid is a disinfectant.

In an eleventh preferred embodiment of the present invention, the ninth preferred embodiment is made so that the first nebulizable liquid is a primary fragrance and the second nebulizable liquid is an accord fragrance for aesthetically enhancing the primary fragrance.

In a twelfth preferred embodiment of the present invention, the second preferred embodiment is made so that the cartridge further comprises a third airless bag for storing a third nebulizable liquid and the interface further includes a third inlet corresponding to the third airless bag, wherein the third inlet provides a path of egress for the third liquid in the third bag so that when the nebulizer operates, the first, second and third nebulizable liquids flow through the interface and are mixed in the space before being nebulized into a combined mist by the nebulizer. In a thirteenth preferred embodiment of the present invention, to the cartridge of the twelfth embodiment is added a fourth airless bag for storing a fourth nebulizable liquid and the interface further includes a fourth inlet, wherein the fourth inlet provides a path of egress for the fourth liquid in the fourth bag so that when the nebulizer operates the first, second, third and fourth nebulizable liquids flow through the interface and are mixed in the space before being nebulized into a combined mist by the nebulizer.

In a fourteenth embodiment of the present invention, a system for refreshing air is provided that comprises at least two air refreshing apparatuses and a power supply. Each individual apparatus includes a base unit, wherein the power supply is operably connected to the base unit; a driving and switching circuit connected to be powered by the power supply; a first plug portion connected to the driving and switching circuit; and a detachable autonomous liquid droplet dispensing cartridge detachably engagable with the first plug portion. The detachable cartridge includes (a) a second plug portion matingly engagable with the first plug portion, (b) a first airless bag for storing a first nebulizable liquid, (c) a second airless bag for storing a second nebulizable liquid, and (d) a casing enclosing the first bag and the second bag. A nebulizer is provided connected to each bag by a respective inlet of an interface, so that, when the nebulizer operates, and first and second liquids are contained in the first and second bags, respectively, the first nebulizable liquid flows from the first bag and the second nebulizable liquid flows from the second bag so that the first nebulizable liquid and the second nebulizable liquid are mixed in a space before being nebulized into a combined mist by the nebulizer. The nebulizer is electrically connected to the power supply and controlled by the driving and switching circuit when the electronic connector engages the cartridge.

In a fifteenth embodiment of the present invention, the system of the fourteenth embodiment is integrated into an HVAC duct.

The sixteenth preferred embodiment of the present invention is a method for refreshing air comprising the steps of (a) providing at least one autonomous liquid droplet dispensing cartridge having multiple airless bags, wherein each bag contains a nebulizable fluid and each bag is connected to an interface, and the interface is connected to a nebulizer, so that there is a path of egress from each bag to the nebulizer through which nebulizable fluid flows to the nebulizer; (b) flowing the nebulizable fluid from each bag to the nebulizer; (c) mixing the nebulizable fluid from each bag in a space to provide a mixed fluid; and (d) nebulizing the mixed fluid to provide a combined mist.

A seventeenth preferred embodiment of the present invention utilizes the steps in accordance with the sixteenth preferred embodiment and further requires that the flow of nebulizable fluid is activated by a signal from a wireless control unit.

An eighteenth preferred embodiment of the present invention utilizes the steps in accordance with the sixteenth preferred embodiment and further requires that nebulizing of the mixed fluid is controlled to maintain a perceived air quality of the ambient air.

Further objects, features and advantages of the present invention will become apparent from the Detailed Description of Preferred Embodiments, which follows, when considered together with the attached drawings.

DETAILED DESCRIPTION OF THE PREFERRED EMBODIMENTS

The present invention is directed to an apparatus and a method for refreshing ambient air and/or air streams in an environment. Typically, the environment is a room or a finite space, or an air stream such as would be present in an HVAC duct, although the present invention is not limited to any one specific environment and can be practiced in relatively open areas. To facilitate an easy understanding of the present invention, the apparatus embodiments in accordance with the present invention will be described first with respect to the drawings, in which like numerals are used to identify like parts.

Figure 1A:
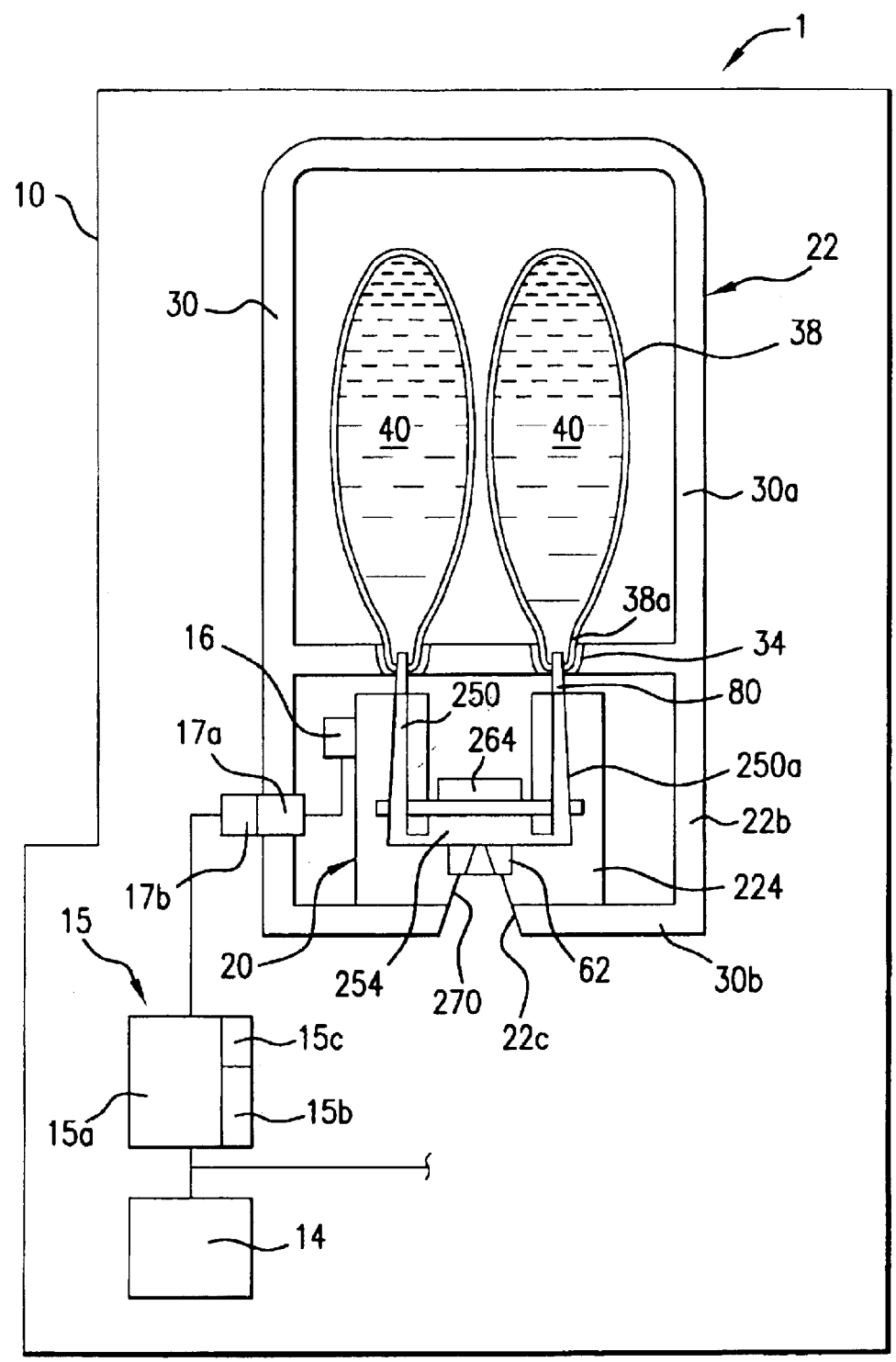
FIG. 1a shows a detailed schematic view of the first preferred embodiment of the apparatus in accordance with the present invention.
Figure 1B:
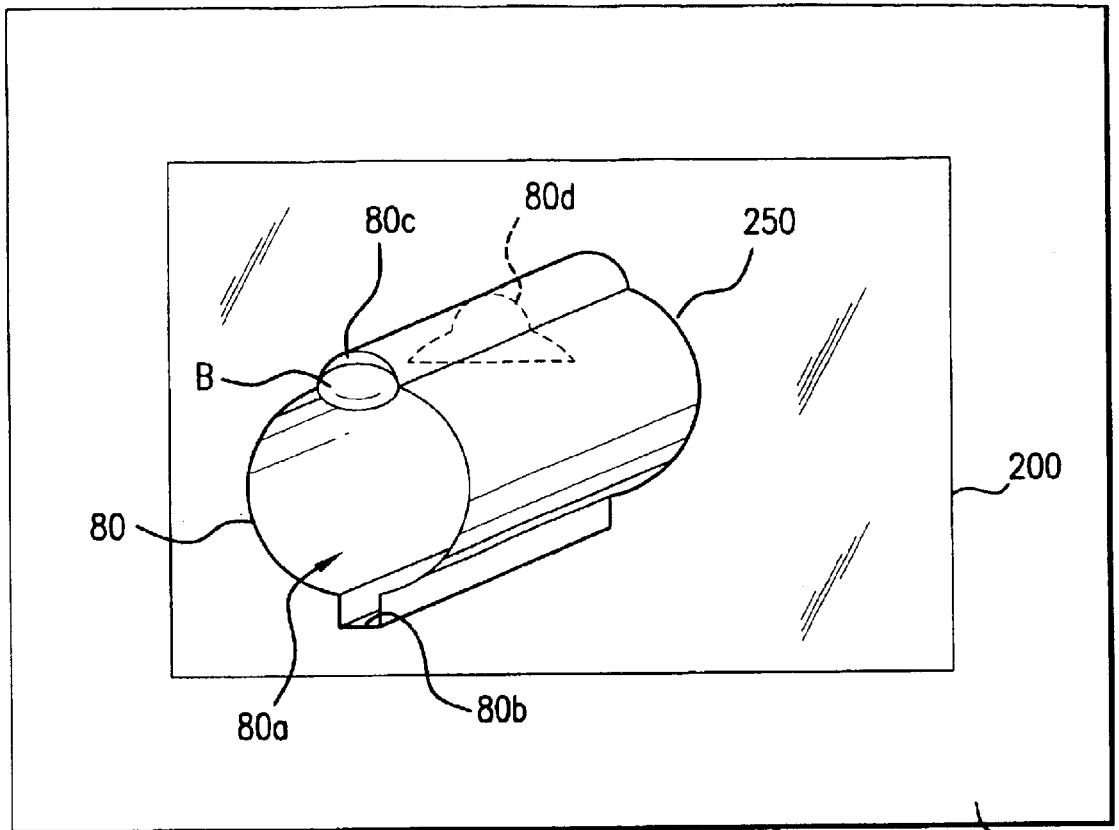
FIG. 1b shows a perspective view of one preferred construction of the liquid pathway in accordance with one preferred embodiment of the present invention.
Figure 1C:
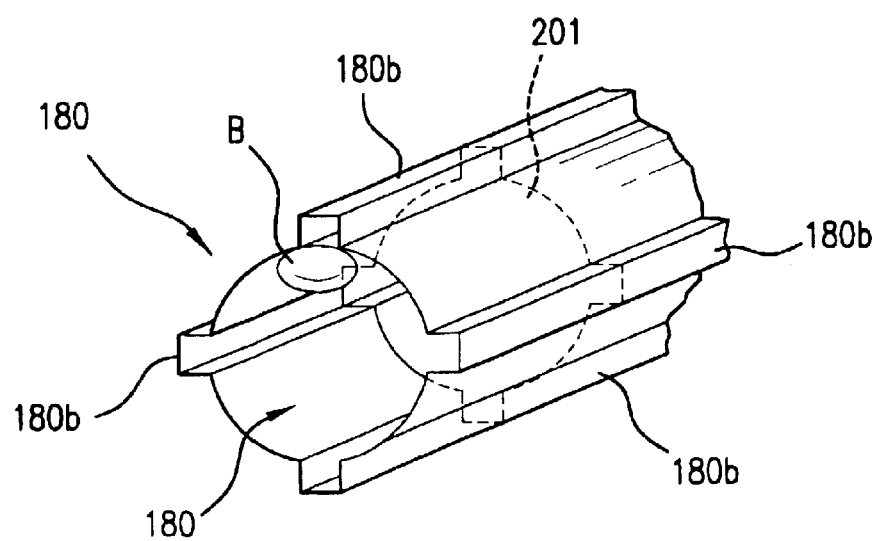
FIG. 1c shows a perspective view of a portion of another preferred construction of the liquid pathway in accordance with another preferred embodiment of the present invention.
Figure 1D:
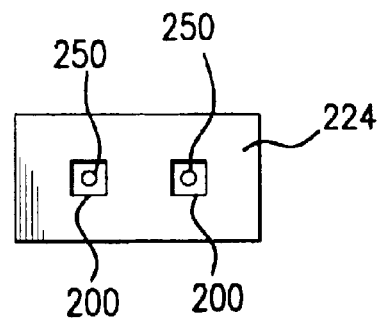
FIG. 1d shows a plan view of the dual interface in accordance with one preferred embodiment of the present invention, wherein inlets are covered by filters.

FIG. 1a schematically illustrates apparatus 1 for refreshing air, a free standing non-limiting preferred embodiment of the present invention. In this context, the term "air" may mean either a body of ambient air or an ambient air stream. Apparatus 1 generally includes a base unit 10 which is a housing, a power supply 14 connected to the base unit, and a driving and switching circuit 15 electrically connected to and powered by power supply 14, such as is disclosed in co-pending U.S. patent application Ser. No. U.S. 09/942,118 and corresponding document EP 00 118 715.2, both of which are incorporated herein by reference in their entirety. Although power supply 14 is shown in FIG. 1a as an internal power supply, the invention is not limited to such and one skilled in the art would appreciate that the power supply could be a plug for connecting to an external power supply or a solar powered cell for example.

Driving and switching circuit 15 includes driver 15a for driving a nebulizer 20 that is connected to a dual autonomous liquid droplet dispensing cartridge 22 via a dual interface 24, and a switch circuit 15b that has a receiving/transmitting portion 15c for receiving an activating electronic signal and transmitting a handshake feedback electronic signal, either wireless or via hard wire, wherein the activating electronic signal is used to activate the switch to start the driver 15a. The electrical circuit shown can preferably be connected to a sensor 16 for detecting, when the nebulizer 20 has run out of fluid to nebulize. Sensor 16 may be a simple fuse that overheats and burns out when nebulizer 20 runs out of liquid to nebulize. Sensor 16 is preferably constructed to be part of cartridge 22. When sensor 16 is activated, the driving and switching circuit IS generates a handshake feedback signal, or in the alternative fails to generate a handshake feedback signal, that is transmitted via portion 15c to a controlling apparatus, as will be described later.

In accordance with one preferred embodiment of the present invention, the autonomous liquid droplet dispensing cartridge 22 is formed integrally by attaching to the airless bags 40 to the interface 224 and nebulizer 20 to form a single integrated replaceable unit. Thus, when cartridge 22 is exhausted, it can be removed from the base unit 10 and replaced with a fresh cartridge. Cartridge 22 includes outer casing 30 that may have portions 30a and 30b for containing one or multiple airless bags 40 and nebulizer 20, respectively. Casing 30 has several access ports 34, and each port has one end 38a of a corresponding autonomous airless bag 38 disposed therein. In this context, the word "autonomous" is meant to convey that the airless bag cartridge is constructed so that the flow of a liquid stored in the bag is air-bubble proof (i.e., not significantly affected by air bubbles in the system) and independent of the position of the cartridge 22. The structure that achieves the autonomous result will be described later.

Casing 30 has disposed on its surface a plug portion 17a for matingly engaging, or plugging into, a corresponding plug portion 17b connected to driving and switching circuit 15. In this manner, it is possible to plug a cartridge 22 into the base unit 10, then unplug the cartridge and replace it with a new one when needed. Casing 30 also includes an opening 22c, so that a nebulized mist generated by the nebulizer 20 can escape the casing.

In each bag 38 there is a fluid 40 stored therein. Each bag 38 may contain the same identical nebulizable liquid; however, preferably, each bag contains a different nebulizable liquid. For example, one bag may contain a primary fragrance and another bag may contain a disinfectant or an insecticide. Another possibility is that one bag may contain a primary fragrance and the other bag may contain a secondary or "accord" fragrance for aesthetically augmenting the primary fragrance. The advantage of having different nebulizable liquids in each bag is that these different liquids can be mixed in a small internal space just prior to nebulization as will be discussed below. Thus, it becomes possible to nebulize liquids that could not be previously used due to storage incompatibility. In other words, some liquids can not be premixed and stored in a single airless bag because either the liquids will form a precipitate or one of the liquids may interfere or degrade the performance of another liquid when stored together.

In a preferred mode of practicing the invention, the fragrances chosen revolve around a central theme or olfactory chord consisting of a primary fragrance around which one or more supporting secondary or accord fragrances are added. For example, several exemplary fragrance themes include a "floral" theme, an "oriental" theme, and a "chypre" theme, although those skilled in the fragrance arts would appreciate that these examples are not limiting to the invention and that there are numerous other fragrance themes that can be used to practice the present invention. Thus, the central declination or primary fragrance would be contained in one of the airless bags. In another airless bag, the varietal declination or accord fragrance would be contained. For example, secondary accord fragrances such as "floral fruity" or "floral green" might be used to augment a primary floral fragrance. Likewise, accord fragrances such as "oriental spicy" and "chypre fruity" respectively could be used to augment corresponding primary oriental and primary chypre fragrances. In this manner, two airless bags can be used to provide a combination of relative fragrance intensities that can be formulated by the perfumer with unprecedented flexibility when mixing fragrances. Consequently, the dual airless bag cartridges in accordance with the present invention allow the user the ability to modulate and experiment with primary and secondary fragrance intensities according to the consumer's particular appreciation and taste. How this is specifically achieved is described later.

Although FIG. 1*a* illustrates a dual airless bag cartridge having two airless bags 38, the cartridge in accordance with the present invention can be practiced wherein the cartridge contains 2, 3, 4 or more airless bags. Preferably, each airless bag has an elongated shape, more cylindrical than spherical, because such an elongated shape has been found to (a) be less sensitive to ambient air pressure, (b) be more compact, (c) provide for a more rigid and durable bag, and (d) is easier to empty fully. The embodiment of the invention which has two bags includes the case where the cartridge has a single bag constructed to have two or more separate and distinct compartments. In other words, a plurality of bags can include a single bag with a plurality of compartments. Each compartment would then have its own corresponding end that is disposed in a respective access port of the casing. The remaining structure of the invention would be the same as is described below. By having one bag with multiple separate compartments, it is still possible to have mixing occur because nebulizable fluid from each compartment can travel through a separate path of egress and then mix in a small internal space prior to nebulization as is discussed below.

FIG. 5 illustrates an autonomous airless bag cartridge 122 that has outer casing 130 that has four access ports 34 and plug portion 17*a*, wherein each port receives one end of an airless bag 38 that is filled with a nebulizable liquid. It would be evident to one skilled in the art that all of the bags 38 could be filled with the same liquid, or each bag could be filled with a different nebulizable liquid than each one of the other bags, or some bags could have the same liquid as some other bags, or the liquid could be different from some of the other liquids contained in one of the other bags. Although not specifically shown, one skilled in the art could make and use the airless bag cartridge to have any number of airless bags or a single bag having any number of compartments. As would be evident from the embodiment of FIG. 5, the cartridge 122 would have a corresponding interface with four inlets used to connect the four airless bags 38 of cartridge 122 to the nebulizer 20.

Having described the dual autonomous liquid droplet dispensing cartridge (i.e., detachable cartridge) in accordance with a preferred embodiment of the present invention, it is useful to describe the interface between the cartridge and the nebulizer. Specifically, FIGS. 1*a* and 2*b* illustrate the basic features of the interface 224. Inlets 250 are formed in the body of interface 224 so that each inlet provides a channel corresponding to one of the access ports 34. Preferably, each inlet 250 is beveled so that the circumference of the cross section of the inlet increases along the path of liquid flow. In this manner, a path of liquid egress is created from the interior of each airless bag 38, through a capillary tube or other short conduit 80 (see FIG. 1*a*), then through the corresponding inlet 250. Typically, the nebulizable liquid is pulled along the path of egress by capillary action, although one skilled in the art would appreciate that a micropump could be used. Once the nebulizable liquid 40 passes through inlet 250, the fluid enters a small internal space 254 for holding the liquid. Space 254 borders the actuator membrane 260 of the nebulizer 20. Nebulizer 20 includes nozzle membrane 62 and an electronically controlled piezo-atomizer 264. The actuator membrane 260 includes peripheral openings 260*a* and forms part of inlets 250 so that liquid can flow into space 254 from the airless bags 40. Typically, when the nebulizer 20 is in operation, a capillary pressure in the inlets 250 will be generated that will tend to draw liquid from each airless bag in the cartridge 22.

In this manner, the liquids contained in the various cartridges 22 will mix in space 254. When the bags 40 contain different liquids such as two different fragrances, or a fragrance in one bag and a functional liquid in another, a unique mixing process occurs as the liquids are nebulized into a mixed or combined nebulized mist.

Figure 3A:
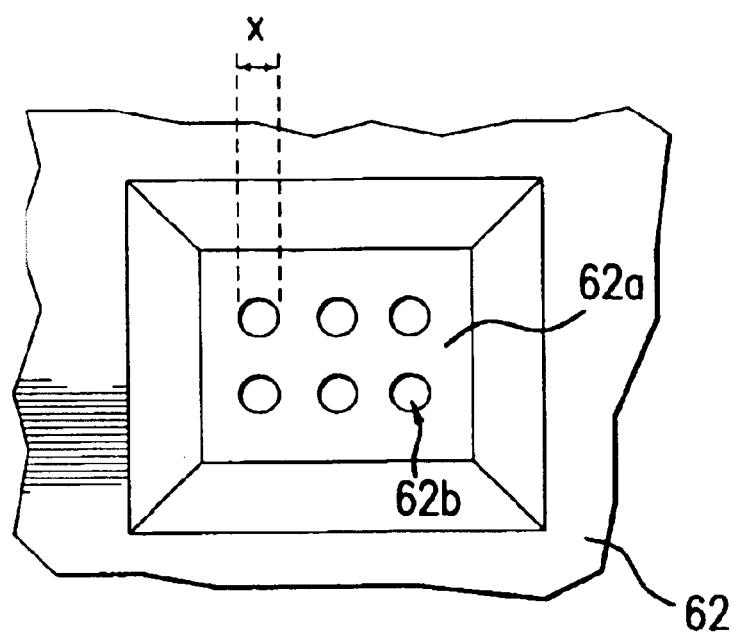
FIG. 3a shows one configuration for a portion of a nozzle membrane usable in the present invention.

As shown in FIG. 3a, the nozzle membrane 62 has a floor portion 62a that includes nozzles 62b, wherein each nozzle is provided by an opening of diameter "x" in the floor portion so that liquid flowing onto the nozzle membrane can be sprayed via nebulization through the nozzles 62b when the nebulizer 20 is in operation. As would be known to one skilled in the art, the nozzles 62b can be sized and configured so that the droplet size dispersion of a nebulized (i.e., atomized) liquid can range from 1 to 7 microns. This droplet size dispersion range is best suited for atomizing ambient scenting or odor-combating liquids.

Figure 3B:
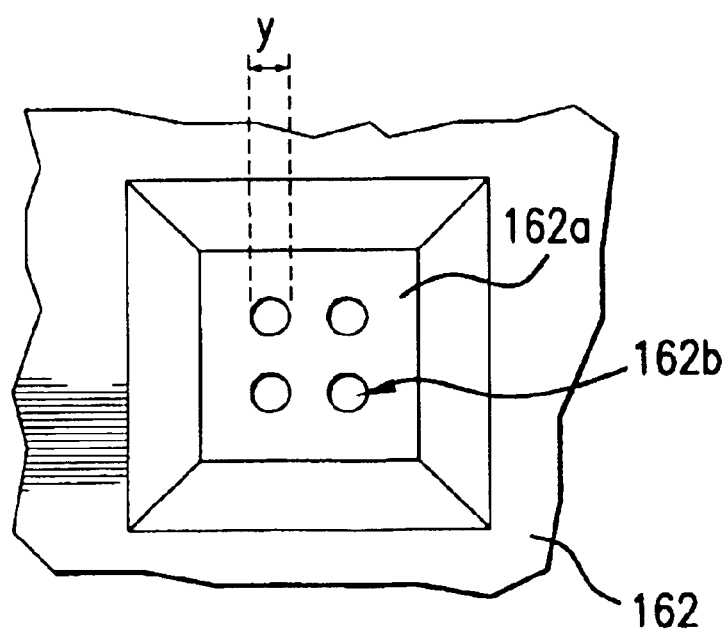
FIG. 3b shows another configuration for a portion of the nozzle membrane usable in the present invention.

On the other hand, as shown in FIG. 3b, the nozzles 162b of floor portion 162a of nozzle membrane 162 in accordance with another embodiment of the present invention, can be formed by openings of diameter "y" that are larger (i.e., y>x) than the openings forming the nozzles 62b of nozzle membrane 62. When the larger openings are used to form nozzles 162b, the nozzles 162b can be sized and configured so that the droplet size dispersion of a nebulized liquid can range from 5 to 30 microns. This droplet size dispersion range is best suited for atomizing disinfectant liquids for local surface disinfecting purposes. This is because a spray plume formed by a nebulized liquid that has a larger droplet size distribution provides a more powerful, albeit more directed, dispersing action such as may be necessary for spraying areas within HVAC ducts and the like with a disinfecting, bacteriostatic, fungistatic, or insecticidal substance. On the other hand, a spray plume that has a smaller droplet size distribution provides faster evaporation and diffusion into the ambient air of fragrance molecules and the like because the spray is finer and has a larger combined surface area that encourages more individual droplets to come in contact with and exchange energy with the ambient air molecules.

One skilled in the art would appreciate that other liquids such as insecticides, etc., can be dispersed by a nebulizer using either one of the nozzle membranes 62 or 162 depending upon which droplet size dispersion range is best suited for the particular spraying application (i.e., whether it is preferable to use directed local surface or volume spraying or rapid dispersion into a relatively large volume of ambient air).

Another advantage of the nozzle membranes used in accordance with the present invention is that the ratio of the total surface of the nebulizer nozzles in contact with the ambient air to the internal surface of the nebulizer (i.e. the surface of the small internal space) is incredibly small so that evaporation through the nebulizer nozzles is negligible and eliminates the need for sealing mechanisms between uses. For example, for a surface A2 corresponding to 144 nozzles with a diameter of 3 microns and an internal nebulizer containing liquid surface A1 of 56.25 mm2, the ratio A2/A1 is 1.8096E-5. For the same number of nozzles, but with a diameter of 12 microns, the ratio is 0.00028953.

Figure 2A:
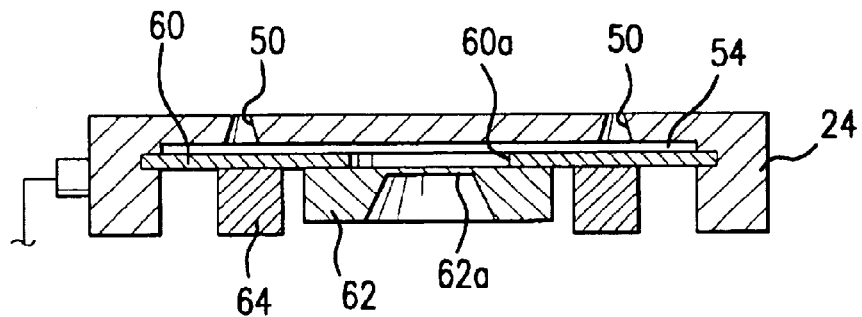
FIG. 2a shows a cross sectional view of a first interface structure between a piezo-atomizer and a dual airless bag cartridge.

FIG. 2a illustrates a first interface structure suitable for use in the present invention. Specifically, interface 24 has inlets 50 formed in the body of the interface that are attached to a conduit 80 and to a corresponding one of the access ports 34. Each inlet 50 is beveled so that the circumference of the cross section of the inlet increases along the path of liquid flow. In this manner, a path of liquid egress is created from the interior of each airless bag 38, through a capillary tube or short conduit 80, then through the corresponding inlet 50. Typically, the nebulizable liquid 40 is pulled along the path of egress by capillary action, although a micropump could be used as well. Once the nebulizable liquid 40 passes through inlet 50, the fluid enters a small internal space 54 for holding the liquid. Space 54 borders the actuator membrane 60 of the nebulizer. The nebulizer includes nozzle membrane 62 and an electronically-controlled piezo-atomizer 64. The actuator membrane 60 includes a central opening 60a so that liquid in space 54 can flow into nozzle membrane 62.

Figure 2B:
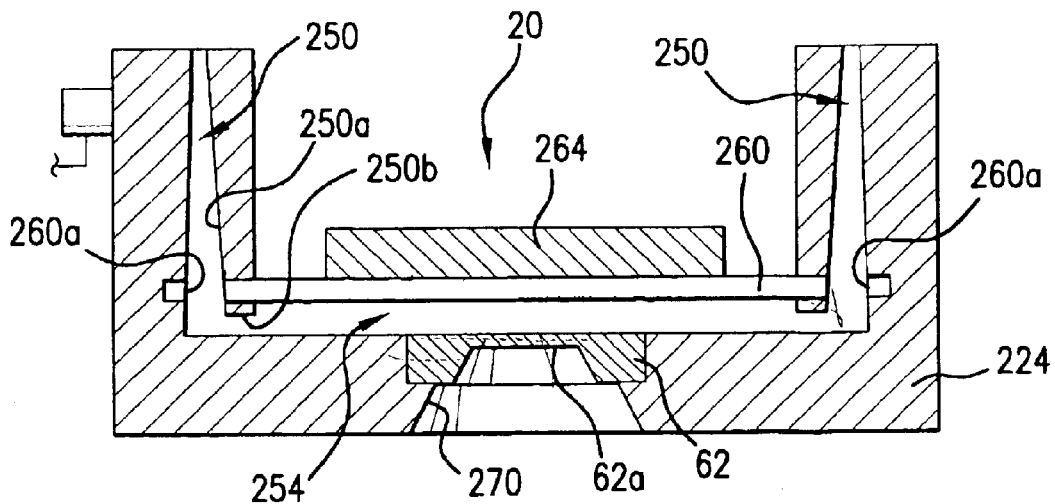
FIG. 2b shows a cross sectional view of a second interface structure between the piezo-atomizer and the dual airless bag cartridge.

FIG. 2b illustrates a preferred second interface structure suitable for use in the present invention. Specifically, interface 224 has inlets 250 formed in the body of the interface; however, the inlets in this structure are roughly L-shaped and have a leg portion 250a that is beveled so that the circumference of the inlet increases along the path of liquid flow. The distal end of leg portion 250a, a point on the leg portion having the largest circumference, is contiguous with the foot portion 250b. Foot portion 250b is contiguous with and opens into space 254. This configuration provides a path of liquid egress from the interior of each airless bag, through a capillary tube or other short conduit, then through the corresponding inlet 250 and into small internal space 254. In this structure, piezo-electric element 264 is disposed on a side of the actuator membrane 260 that is opposite to the side of the actuator membrane near which the nozzle membrane 62 is disposed. In interface 24, the piezo-electric element 64 is disposed on the same side of actuator membrane 60 as is the nozzle membrane 62. In interface 224, actuator membrane 260 has no central opening but instead has two peripheral openings 260a that form a portion of inlets 250. Also, the body of interface 224 includes a large beveled cavity 270, which forms a sort of nozzle through which the nebulized liquid would pass after it has been nebulized through the nozzle membrane 62.

Figure 2C:
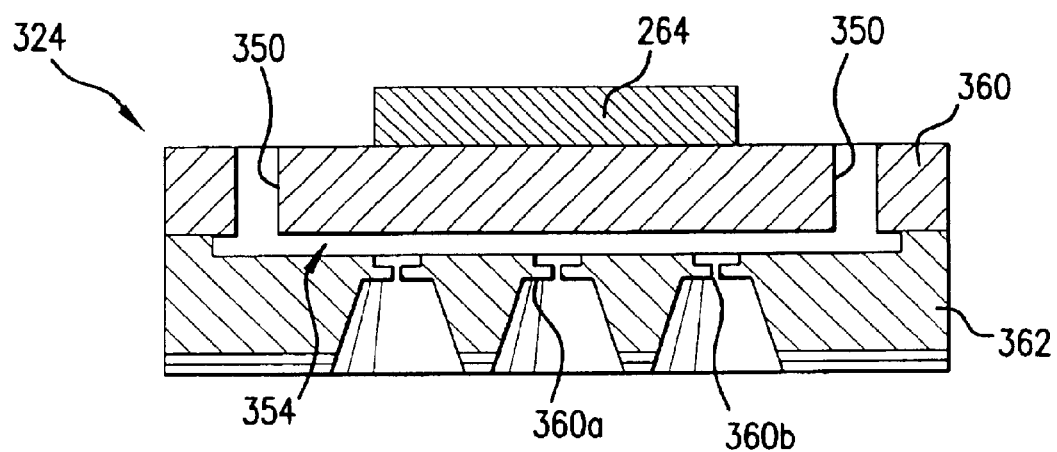
FIG. 2c shows a cross sectional view of third interface structure between the piezo-atomizer and the dual airless bag cartridge.

FIG. 2c illustrates a preferred third interface structure suitable for use in the present invention. Specifically, the third interface structure 324 is disclosed in U.S. Pat. No. 6,196,219 B1 to Hess et al., which is incorporated herein in its entirety by reference, as well as in co-pending application EP 01 121 075.4 and EP 01 103 653.0, both to Hess et al., both of which are likewise incorporated herein by reference. This interface 324 includes actuator membrane 360 that has inlets 350 formed therein. The inlets 350 are contiguous with small internal space 354 for holding the liquid to be nebulized and correspond in number to the number of access ports 34 of the cartridge 22. The piezo-electric element 264 is disposed on one side of the actuator membrane 360 and the nozzle membrane 362 is disposed on the other side of the actuator membrane. The advantage of the interface 324 is that the nozzles 362b of floor portions 362a are located to coincide with standing wave crests that are generated when the piezo-electric element 264 is activated, thereby increasing the nebulization efficiency of the liquid being nebulized.

The main advantage of the three described interface structures is that a dual or multiple inlet connection is provided that interfaces well with the innovative dual airless bag cartridges of the present invention to insure generally uniform filing of the inlets and spaces of the interface structure. Another advantage is that the small internal space can be constructed to be minimized in size with parallel upper and lower internal surfaces for holding and transmitting energy to the liquid to be atomized. In this context, the present invention can achieve an internal space with parallel upper and lower internal surfaces wherein the distance, or height, separating the upper and lower surfaces is preferably less than 100 microns, or optimally between 10 to 60 microns. The benefit of minimizing the size of the internal space and having parallel upper and lower surfaces is that the nebulizer can operate using nebulizable liquids over a very large range of viscosities and surface tensions, which allows the apparatus to use largely solvent-free nebulizer liquid formulations while at the same time providing an unprecedented flexibility in the formulation of scenting and disinfecting liquids.

Another important feature in accordance with the present invention is that the dual airless bag cartridge is essentially air-bubble proof and position independent. In other words, the nebulizable liquids stored in the cartridge are relatively unaffected by any air bubbles that get into the airless bags and are unaffected by the position of the apparatus. This feature is achieved by the structures shown in FIG. 1*b*, 1*c* and 1*d*.

Specifically, FIG. 1*b* illustrates a liquid pathway 80, being either a capillary tube or other short fluid conduit, that connects the interior of airless bag 38 to the mouth of the respective inlet 250 on the interface 224. Of course, this liquid pathway structure can be applied to the inlets 50 of interface 24 or the inlets 350 of interface 324. In this embodiment, the liquid pathway is constructed to have a main flow path 80a and a single radial groove 80*b*. Generally, fluid flows from the airless bag through the main flow path 80*a* and into the respective inlet of the interface. However, if an air bubble occludes this pathway, the fluid may still bypass the obstruction via the radial groove 80*b*. This occurs because any obstructing bubble will be generally spherical and will not conform to obstruct both the main flow path and the radial groove simultaneously. In addition, pathway 80 can be constructed to include a domed bubble trap portion 80*c* for trapping a bubble B that might get into the pathway. The trap portion 80*c* is curved to trap a bubble. In addition, a bubble filter and/or antimicrobial filter 200 can be disposed to cover the inlet 250 so that the pathway 80 is disposed on the surface of the filter 200. As another precautionary measure, an air evacuating filter 80d can be integrated inside the interior of pathway 80 so that the filter 80*d* covers the entire cross sectional area of the interior of the pathway. In addition, the filter 80*d* may be constructed to cover only a portion of the cross sectional area of the interior of the pathway, such as the interior of the domed trap portion 80*c*. As would be appreciated by one skilled in the art, the liquid pathway 80 can be constructed to be connected at one end to an access port 34 of cartridge 22 and connected at the other end to a corresponding inlet of the interface.

FIG. 1*c* illustrates an alternate embodiment of the liquid pathway. Specifically, liquid pathway 180 includes a main flow path 180*a* and four radial grooves 180*b*. Having four radial grooves increases the rate of bypassing fluid flow through the grooves when the main flow path is obstructed or partially obstructed by a bubble (B). As would be appreciated by one skilled in the art, it is possible to make the liquid pathway to have any number of radial grooves for promoting bypass liquid flow should the main pathway become obstructed, although preferably from 1 to 4 radial grooves are used.

FIG. 1*d* shows that bubble filters and/or antimicrobial filters 200 can be disposed over the inlets 250 of the interface 224 to further decrease the chance that a bubble and/or an overgrowth of microbes will obstruct the path of liquid egress between the airless bags and the small internal space for holding the liquid to be nebulized. Of course, these filters 200 can be applied to the inlets 50 of interface 24 or the inlets 350 of interface 324. In addition, one skilled in the art would appreciate that bubble filters and/or antimicrobial filters 201 can be disposed inside of the main flow path liquid pathway 180 (or 80), and near the corresponding inlet.

In another embodiment in accordance with the present invention, a system for refreshing air 400 as shown in FIG. 4*a* comprises two or more apparatuses 1*a* that are electronically connected in parallel to a common power supply 14*a* via hard wire 402. Each apparatus 1*a* is identical to the embodiment of apparatus 1 except the power supply 14 has been replaced by a suitable electronic connector 5*a* such as a plug system so that each apparatus 1*a* can be connected to the power supply 14*a*. In addition, each apparatus 1*a* is operationally connected to a driving and switching circuit 5*b* housed in a base unit, wherein the driving and switching circuit 5*b* includes a receiving/transmitting portion that is similar to the receiving/transmitting portion 15*c* as described previously for another embodiment of the invention. However, in the system 400 it is preferable that the receiving/transmitting portion of the driving and switching circuit 5*b* be an electronic receiver/transmitter for receiving/transmitting wireless electronic signals from/to wireless control unit 405 such as a personal digital assistant (PDA), cellular phone, a web-appliance or the like. Plainly, other wireless devices for generating the wireless switching signal can be used, and it is within the scope of the present invention to transport the switching signal via a hard wire.

It should be noted that there is no need for an on-board memory chip and/or microcontroller in the autonomous cartridges because the control and memory functions are provided by the wireless control unit 405. This is a great advantage over many of the prior cartridges.

FIG. 4*b* illustrates one particular wireless control unit that is well suited for use in the embodiment of the invention described in FIG. 4*a*. Specifically, wireless control unit 500 is a hand held remote control unit as is generally known in the art. In particular, wireless control unit 500 includes a wireless signal transmitter/receiver 556 for transmitting and receiving wireless electronic signals to and from the driving and switching circuits 5*b* of one or more apparatuses 1*a*. In addition, each apparatus la may include a small fan (not shown) that is used to generate additional ambient air flow for dispersing any nebulized mist, and the control unit 500 can be wired to communicate with the apparatus 1*a* so as to operate the fan for each of the one or more apparatuses 1*a* networked into system 400.

Control unit 500 also includes a gas sensor 551, a turbulence detector 552, and a presence sensor (not shown). Gas sensor 551 is a logarithmically calibrated electronic sensor that detects and "memorizes" the intensity of scents (i.e., fragrances) in the ambient air. In this context, the sensor 551 is used to "memorize" the intensity of scents by recalibrating the sensor 551 to a particular scent intensity desired by the user of the control unit 500. In other words, a user can operate the control unit 500 by means of intensity control keys 554 and input keys 555, as is generally well known in the art of remote control. Thus, the sensor 551 can be set by the user using SMS language or the like to detect scents that are calibrated to be very high (VHI), high (HI), medium high (MI), ok (OKI), low (LI), medium low (MLI), or very low (VLI) intensity, wherein the display 553 can indicate the selected gas sensor calibration level as a bar graph 553*a* for the user. Of course, control unit 500 is not limited to the use of bar graphs, and one skilled in the art would realize that alphanumeric indicia, pie graphs, line graphs, etc., could be used to display the selected gas sensor calibration level.

Control unit 500 also includes a turbulence detector 552 for indicating the intensity of air flow at the point of detection (i.e. the point of scent appreciation) chosen by the user. In other words, the user may carry the control unit to a particular location in a room or enclosed space and use this location as the point of detection. The turbulence detector 552 can also be wired to activate a small fan in each of the operating apparatuses 1a by means of the transmitter/receiver 556 and the driving and switching circuit 5b so as to provide a more rapid and efficient diffusion of the nebulized liquid throughout the room or enclosed space.

Control unit 500 can also be provided with a presence detector to complement the functions of the gas and turbulence sensors. The presence detector would activate the system 400 when an individual encroached within a certain range of the presence detector, thereby minimizing the on-time delay of the system 400 and avoiding the wastage of nebulizable liquid into the room or enclosed space when no one is there.

Control unit 500 is provided with internally preprogrammed electronic circuitry that includes several software programs. First, calculation software calculates a coefficient of "perceived air quality," expressed in SMS language or the like, based upon inputs from the turbulence detector 552 and the gas sensor 551, then maintains the "perceived air quality" level via cyclic readings of the gas sensor 551 that detects the intensity of scents in the ambient air so that the intensity of the nebulized fragrances in the ambient air is maintained between the "perceived air quality" intensity (maximum intensity) and a minimum intensity level programmed by the user of the control unit 500. In this case, the minimum intensity level is one of the selected gas sensor calibration levels such as "MI" or "VLI" for example.

When control unit 500 is shut off by either the user or the presence sensor, the software of the control unit will reactivate when either the presence sensor indicates that someone has entered into the sensor's proximity detection range, or when the user activates the unit. Upon reactivation, control unit 500 automatically reactivates system 400 to operate the apparatuses 1a until the previously set "perceived air quality" level is reached and maintained. Thus, the software of control unit 500 operates the system 400 to provide ambient air refreshing based on the intelligent networking of the flexible, autonomous liquid atomizer cartridges.

The software described above can be ported via a suitable interface to work with other remote control units such as a personal digital assistant, a personal computer, a tablet computer, a web-appliance, a cellular phone, a stand-alone household appliance, and the like. In the alternative, the software may be preprogrammed into a remote control unit for an HVAC system, or the control unit may have the turbulence sensor positioned remotely from the control unit and inside an HVAC duct.

In a preferred embodiment of the invention, the software for use in the control unit 500 includes a fuzzy logic algorithm to deal with the qualitative terms and values, to memorize settings for certain values of turbulence, and to include a learning capability to optimize the performance and efficacy of the air refreshing process. Of course, one skilled in the art would recognize that the system 400 could be networked into several different rooms or enclosed spaces and that one or more control units 500 could be used to adjust the "perceived air quality" separately in each of the rooms or enclosed spaces in the network.

Figure 4A:
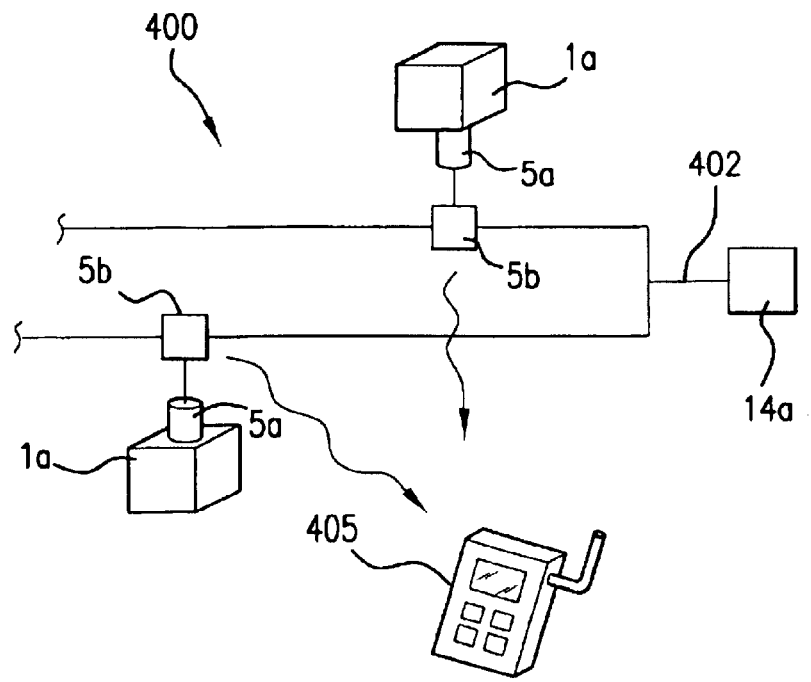
FIG. 4a shows the networked system for refreshing air as another embodiment of the present invention.
Figure 4B:
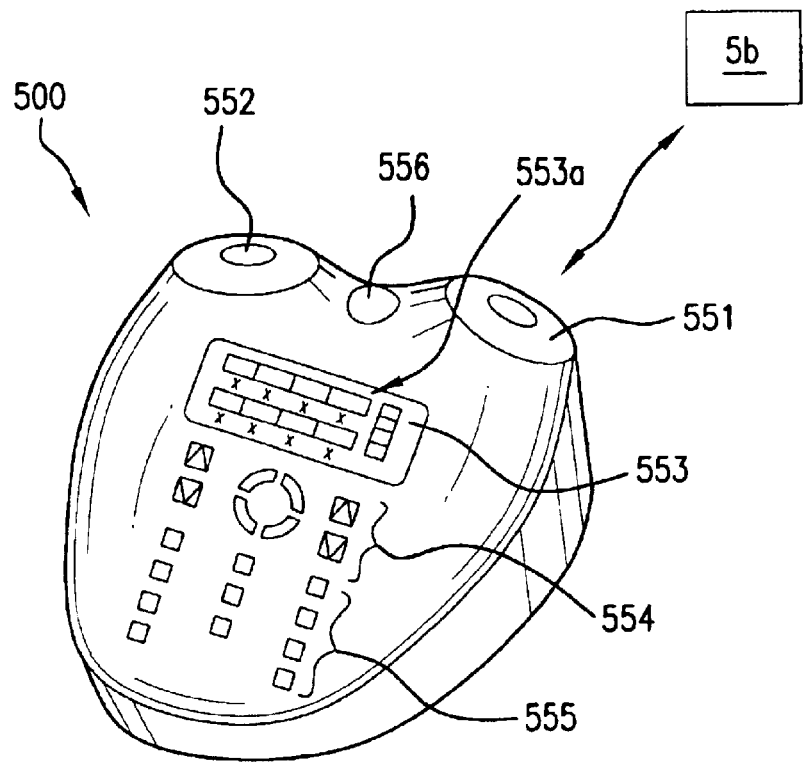
FIG. 4b shows a particular wireless control unit for use in the present invention.
Figure 5:
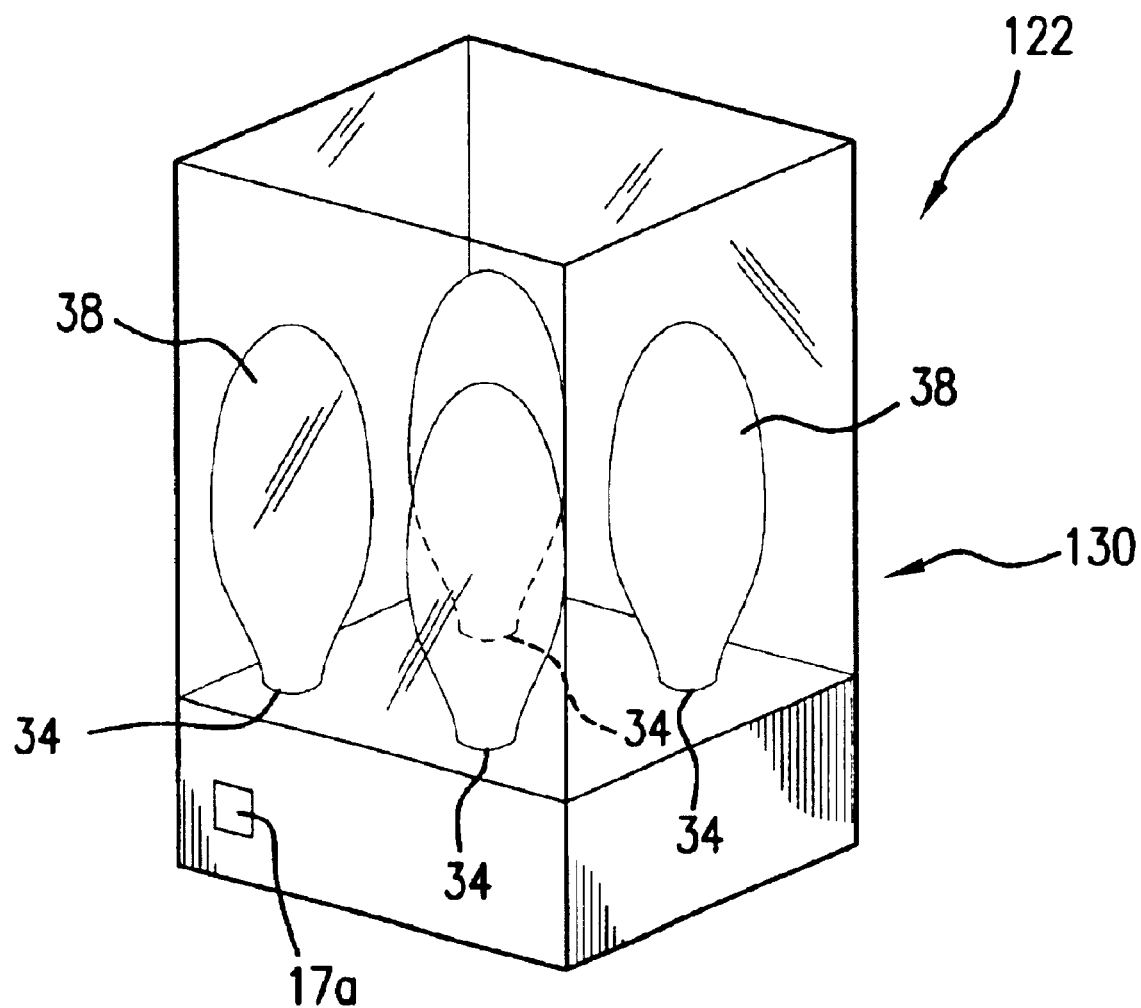
FIG. 5 shows an apparatus for refreshing air in accordance with a preferred embodiment of the present invention wherein the cartridge has four airless bags.

The embodiment of the invention illustrated in FIG. 4a is especially suited to be installed in a built-in Indoor Air Quality system network such as is used in larger private and public buildings, or as might be used for HVAC duct disinfecting. For example, one or more of the apparatuses 1a can be positioned inside an HVAC duct and operated in conjunction with the central or remote control of the HVAC system, one or more airflow sensors in the duct system, and the wireless remote control unit 405.

Another preferred embodiment of the present invention as illustrated in FIG. 1a provides a portable, stand-alone device with at least one cartridge. These devices can be constructed for installation in a variety of environments such as private and public bathrooms, clothing, linen or kitchen cabinets, or on home or office furniture. These portable devices can be operated by a pushbutton, or by a signal such as provided by a presence sensor or a timer circuit, or by a signal from a network or remote control device. In addition, these devices can be added to luxury or practical items, being added as accessories to lamps, furniture or built into vacuum cleaners, white goods, cars, household robots or other useful and fun items. The power supply can be batteries, small fuel cells, main power supplies, car batteries, etc.

In another particular embodiment of the invention, a cartridge with a small dual airless bag of, for example, more or less 1 ml of fluid in each airless bag can be fitted into a fashion accessory such as a broche or bracelet, watch, necklace pendant, or other jewelry, or as an integrated part of clothing such as a lapel or other part of a garment. In this case, the power supply is preferably 2 "AA" batteries and the circuit includes a very small driving and switching circuit that can be hidden in a small pocket inside the user's clothing. Thus, the power supply in connection with the driving and switching circuit can be connected to the cartridge via a miniature version of the plug system 5a and a thin cable. Thus, a personal, wearable "on-demand" ambient scenting device with plug-in type exchangeable cartridges is provided either as a fashion accessory or for wear with a fashion accessory. Activation of the device can be via a touch button or via remote short distance wireless signals such as a phonetic or sensor based input.

In a variant of this embodiment, the air refreshing wearable device could be constructed to be activated by a specific portable phone or other specific communication devices as a form of a noiseless, vibrationless fragrant contact message that serves the same purpose as ringing does for a telephone. Thus messages for "confidential" callers having a particular calling identity can be made using wireless technology, Bluetooth™, or other technology such as can be accessed from a portable phone or other communication device.

In another variant of this embodiment, the air refreshing wearable device can be incorporated as a message indicator for a portable phone or other communication device, where the fragrance released serves the as a silent "ring."

In another variant of this embodiment, the power supply, driving and switching circuit and exchangeable cartridge are integrated into an alarm clock, thereby allowing inhabitants of a room or small enclosed space to wake up to fragrance. In addition, two or more scent combinations can be generated using a network system integrated into the clock so that two or more difference fragrance combinations can be used to wake up different people at different times. In addition, the fragrance emission could be accompanied by an initially weaker but progressively intensifying sound.

It is self evident that the system 400, comprising two or more apparatuses 1a, will include a corresponding number of cartridges 22. In the case where multiple cartridges are used, it is plain that the present invention will provide the consumer with the ability to choose not only a central ambient fragrance or theme based upon a primary fragrance, but the consumer has the option to create a fragrance ensemble by selecting more than one primary fragrance to be nebulized at one time by using a PDA. Furthermore, the consumer has the ability to choose from a larger number of secondary or accord fragrances. For example, the user could choose one or more primary oriental fragrances to create an "oriental ensemble," then augment this ensemble by nebulizing one or more varietal declinations or accords to the ensemble. In this example, the user may choose to use a "spicy oriental" fragrance. Or the user could choose to mix one or more central fragrance concepts (i.e., primary fragrances) with or without adding any varietal declinations (i.e., accord fragrances).

To illustrate more clearly, in the case where the system has only two dual airless bags (i.e., there are only two apparatuses connected in the system) then it is possible to have two different primary fragrance concepts with one accord each or, in the alternative, two different accords to the same fragrance concept could be offered. However, it is also possible to valve the airless bags individually (not shown) so that only one bag or both bags are used to provide liquid to the nebulizer. One skilled in the art could construct a valve system of one or more valves connected to and controlled by the driving and switch circuit 15. In the case where the cartridge includes 3, 4 or more airless bags filled with various liquids, the valve system can permit the airless bags to be individually accessed for liquid so that only one bag, or several bags, or all of the bags are accessed to provide liquid to the nebulizer. In this manner, it is possible to provide an even greater variety of fragrance and/or functional liquid content mixes to the nebulizer.

Another variation afforded by the structure of the present invention is that the nebulizable fluids used include fragrances and/or functional liquids. For example, the system could include an apparatus 1a containing a primary fragrance and an accord fragrance, and another apparatus 1a could contain the functional liquid such as a disinfecting, bacteriostatic or fungistatic liquid. Thus, it is possible to effectively disperse a bactericide or fungicide using the present invention by using suitable chemical ingredients such as Bronopol and to combine the corresponding compound with a suitable fragrance. However, it is preferable to use fragrance compounds that are known to have disinfecting, bacteriostatic, or fungistatic properties and to place them in the first airless bag of the cartridge and to put a purely ambient fragrance compound into a second airless bag of the same cartridge. In this manner, the purely ambient fragrance can be used as the accord fragrance for augmenting the primary fragrance of the fragrance having disinfecting, bacteriostatic, or fungistatic properties.

This same concept holds true for insect repellants, other functional nebulizable liquids and other individual fragrance notes. In this manner, by using fragrances that have functional properties as well it is possible to minimize the use of potentially harmful benzenes, toluenes, like compounds, and other industrial solvents because the dual airless bag cartridge system in accordance with the present invention provides for greater flexibility and more precise formulation of air freshening mixtures. Thus, the dosing precision of the refreshing mixtures is optimized so that excess amounts of potentially harmful substances are avoided.

Lastly, the method embodiment in accordance with the present invention is a method for refreshing air summarized to include the steps of: (a) providing at least one autonomous liquid droplet dispensing cartridge having multiple airless bags, wherein each bag contains a nebulizable fluid and each bag is connected to an interface, and the interface is connected to a nebulizer, so that there is a path of egress from each bag to the nebulizer through which nebulizable fluid flows to the nebulizer; (b) flowing the nebulizable fluid from each bag to the nebulizer; (c) mixing the nebulizable fluid from each bag in a space to provide a mixed fluid; and (d) nebulizing the mixed fluid to provide a combined mist as is evident from the previous description of the apparatus embodiments. Of course, the method can be further refined to include that the flow of nebulizable fluid is activated by a signal from a wireless control unit. The method can also be refined to include that nebulizing of the mixed fluid is controlled to maintain a perceived air quality of the ambient air.

While the present invention has been described with reference to certain preferred embodiments, one of ordinary skill in the art will recognize that additions, deletions, substitutions, modifications and improvements can be made while remaining within the spirit and scope of the present invention as defined by the appended claims.

What is claimed is:

1. An apparatus for freshening air, the apparatus comprising:
   a base unit;
   a power supply operably connected to the base unit;
   a driving and switching circuit connected to be powered by the power supply;
   a first plug portion connected to the driving and switching circuit;
   a detachable autonomous liquid droplet dispensing cartridge detachably engagable with the first plug portion, having
     (a) a second plug portion matingly engagable with the first plug portion,
     (b) a first airless bag for storing a first nebulizable liquid
     (c) a second airless bag for storing a second nebulizable liquid, and
     (d) a casing enclosing the first bag and the second bag; and
   a nebulizer connected to each bag by a respective inlet of an interface, so that, when the nebulizer operates, and first and second nebulizable liquids are contained in the first and second bags, respectively, the first nebulizable liquid flows from the first bag and the second nebulizable liquid flows from the second bag so that the first nebulizable liquid and the second nebulizable liquid are mixed in a space before being nebulized into a combined mist by the nebulizer;
   wherein the nebulizer is electrically connected to the power supply and controlled by the driving and switching circuit when the second plug portion is matingly engaged to the first plug portion.

2. An apparatus for refreshing air as recited in claim 1, wherein the interface includes a first inlet that provides a path of egress for the first liquid and a second inlet that provides a path of egress for the second liquid, so that, when the nebulizer operates, and first and second nebulizable liquids are contained in the first and second bags, respectively, the first nebulizable liquid and the second nebulizable liquid flow from the first bag and the second bag, respectively, through the interface and into the nebulizer.

3. An apparatus for refreshing air as recited in claim 1, wherein the nebulizer includes a nozzle membrane that has at least one nozzle sized to disperse droplets that are about 1–7 microns in diameter.

4. An apparatus for refreshing air as recited in claim 1, wherein the nebulizer includes a nozzle membrane that has at least one nozzle sized to disperse droplets that are about 5–30 microns in diameter.

5. An apparatus for refreshing air as recited in claim 2, further comprising a switch disposed in the driving and switching circuit and electrically connected to the power supply,
   wherein the switch activates the nebulizer and the flow of the first nebulizable liquid and the second nebulizable liquid from the first airless bag and the second airless bag, respectively, through the interface and into the nebulizer.

6. An apparatus for refreshing air as recited in claim 5, wherein the switch is operable by a remote unit.

7. An apparatus for refreshing air as recited in claim 6, wherein the remote unit is a wireless control unit, a personal digital assistant, a cell phone, or a web-appliance.

8. An apparatus for refreshing air as recited in claim 6, wherein the remote unit includes a turbulence sensor for sensing the flow of ambient air and a logarithmic gas sensor for detecting the combined concentration of the first nebulizable liquid and the second nebulizable liquid in the ambient air.

9. An apparatus for refreshing air as recited in claim 1, wherein the first bag contains a first nebulizable liquid that is different from a second nebulizable liquid contained in the second bag.

10. An apparatus for refreshing air as recited in claim 9, wherein the first nebulizable liquid is a primary fragrance and the second nebulizable liquid is a disinfectant.

11. An apparatus for refreshing air as recited in claim 9, wherein the first nebulizable liquid is a primary fragrance and the second nebulizable liquid is an accord fragrance for aesthetically enhancing the primary fragrance.

12. An apparatus for refreshing air as recited in claim 2, wherein the cartridge further comprises a third airless bag for storing a third nebulizable liquid and the interface further includes a third inlet corresponding to the third airless bag, wherein the third inlet provides a path of egress for the third liquid in the third bag so that when the nebulizer operates, and first, second and third nebulizable liquids are contained in the first, second and third bags, respectively, the first, second and third nebulizable liquids flow through the interface and are mixed in the space before being nebulized into a combined mist by the nebulizer.

13. An apparatus for refreshing air as recited in claim 12, wherein the cartridge further comprises a fourth airless bag for storing a fourth nebulizable liquid and the interface further includes a fourth inlet, wherein the fourth inlet provides a path of egress for the fourth liquid in the fourth bag so that when the nebulizer operates, and first, second, third and fourth nebulizable liquids are contained in the first, second, third and fourth bags, respectively, the first, second, third and fourth nebulizable liquids flow through the interface and are mixed in the space before being nebulized into a combined mist by the nebulizer.

14. A system for refreshing air comprising at least two air refreshing apparatuses and a power supply, wherein each apparatus comprises:
   a base unit, wherein the power supply is operably connected to the base unit;
   a driving and switching circuit connected to be powered by the power supply;
   a first plug portion connected to the driving and switching circuit;
   a detachable autonomous liquid droplet dispensing cartridge detachably engagable with the first plug portion, having
   (a) a second plug portion matingly engagable with the first plug portion,
   (b) a first airless bag for storing a first nebulizable liquid
   (c) a second airless bag for storing a second nebulizable liquid, and
   (d) a casing enclosing the first bag and the second bag; and
   a nebulizer connected to each bag by a respective inlet of an interface, so that, when the nebulizer operates, and first and second liquids are contained in the first and second bags, respectively, the first nebulizable liquid flows from the first bag and the second nebulizable liquid flows from the second bag so that the first nebulizable liquid and the second nebulizable liquid are mixed in a space before being nebulized into a combined mist by the nebulizer,
   wherein the nebulizer is electrically connected to the power supply and controlled by the driving and switching circuit when the first plug portion engages the cartridge.

15. A system for refreshing air as recited in claim 14, wherein the system is integrated into an HVAC duct.

16. A method for refreshing air comprising the steps of:
   (a) providing an apparatus for freshening air, the apparatus comprising
   a base unit;
   a power supply operably connected to the base unit;
   a driving and switching circuit connected to be powered by the power supply;
   a first plug portion connected to the driving and switching circuit;
   a detachable autonomous liquid droplet dispensing cartridge detachably engagable with the first plug portion, having
      (1) a second plug portion matingly engagable with the first plug portion,
      (2) a first airless bag for storing a first nebulizable liquid
      (3) a second airless bag for storing a second nebulizable liquid, and
      (4) a casing enclosing the first bag and the second bag; and
   a nebulizer connected to each bag by a respective inlet of an interface, so that, when the nebulizer operates, and first and second nebulizable liquids are contained in the first and second bags, respectively, the first nebulizable liquid flows from the first bag and the second nebulizable liquid flows from the second bag so that the first nebulizable liquid and the second nebulizable liquid are mixed in a space before being nebulized into a combined mist by the nebulizer,
   wherein the nebulizer is electrically connected to the power supply and controlled by the driving and switching circuit when the second plug portion is matingly engaged to the first plug portion;
   (b) flowing the nebulizable liquid from each bag to the space;
   (c) mixing the nebulizable fluid from each bag in the space to provide a mixed fluid; and
   (d) nebulizing the mixed fluid to provide a combined mist.

17. A method for refreshing air as recited in claim 16, wherein the flow of nebulizable fluid is activated by a signal from a wireless control unit.

* * * * *